US012743942B2

(12) United States Patent
Birch et al.

(10) Patent No.: US 12,743,942 B2
(45) Date of Patent: Sep. 22, 2026

(54) METHOD AND SYSTEM FOR CONFIRMATION OF VIRAL SAFETY STATUS

(71) Applicant: 13482073 CANADA INC., Markham (CA)

(72) Inventors: Peter Birch, Markham (CA); Ching Kuo Pai, Markham (CA)

( * ) Notice: Subject to any disclaimer, the term of this patent is extended or adjusted under 35 U.S.C. 154(b) by 1146 days.

(21) Appl. No.: 17/737,330

(22) Filed: May 5, 2022

(65) Prior Publication Data

US 2023/0293756 A1 Sep. 21, 2023

Related U.S. Application Data

(63) Continuation-in-part of application No. 17/718,404, filed on Apr. 12, 2022, which is a continuation-in-part of application No. 17/699,488, filed on Mar. 21, 2022, now Pat. No. 12,559,370.

(51) Int. Cl.

| | |
|---|---|
| ***G08B 21/18*** | (2006.01) |
| ***A61L 9/015*** | (2006.01) |
| ***G07C 9/32*** | (2020.01) |
| *A61L 9/20* | (2006.01) |
| *G08B 17/00* | (2006.01) |

(52) U.S. Cl.

CPC ............ *G08B 21/182* (2013.01); *A61L 9/015* (2013.01); *G07C 9/32* (2020.01); *A61L 9/20* (2013.01); *G08B 17/00* (2013.01)

(58) Field of Classification Search

CPC ........ G08B 17/00; G08B 17/06; G08B 17/10; G08B 21/10; G08B 21/18; G08B 21/182; G08B 25/10; G07C 9/32; A61L 9/00; A61L 9/015; A61L 9/20

See application file for complete search history.

(56) References Cited

U.S. PATENT DOCUMENTS

| | | | | |
|---|---|---|---|---|
| 2013/0117078 | A1* | 5/2013 | Weik, III | B60R 25/00 705/13 |
| 2015/0287310 | A1* | 10/2015 | Deliuliis | G08B 25/10 340/628 |
| 2018/0315301 | A1* | 11/2018 | Subramanian | G06V 10/765 |
| 2024/0288381 | A1* | 8/2024 | Stowell | H01Q 13/20 |

* cited by examiner

*Primary Examiner* — Van T Trieu

(57) ABSTRACT

A method and system of monitoring viral safety status associated with entry into a facility. The method comprises receiving, at a display user interface rendered at a mobile computing device, a selection of indicia representative of the facility, receiving, responsive to the selection, an ozone gas viral cleaning status of the facility, determining, based on the ozone gas viral cleaning status and at least one threshold entrant condition in association with an entrant category, a suitability for entrance into the facility and generating, at the display user interface, a notification in accordance with the suitability for entrance.

20 Claims, 11 Drawing Sheets

300

Figure 4:
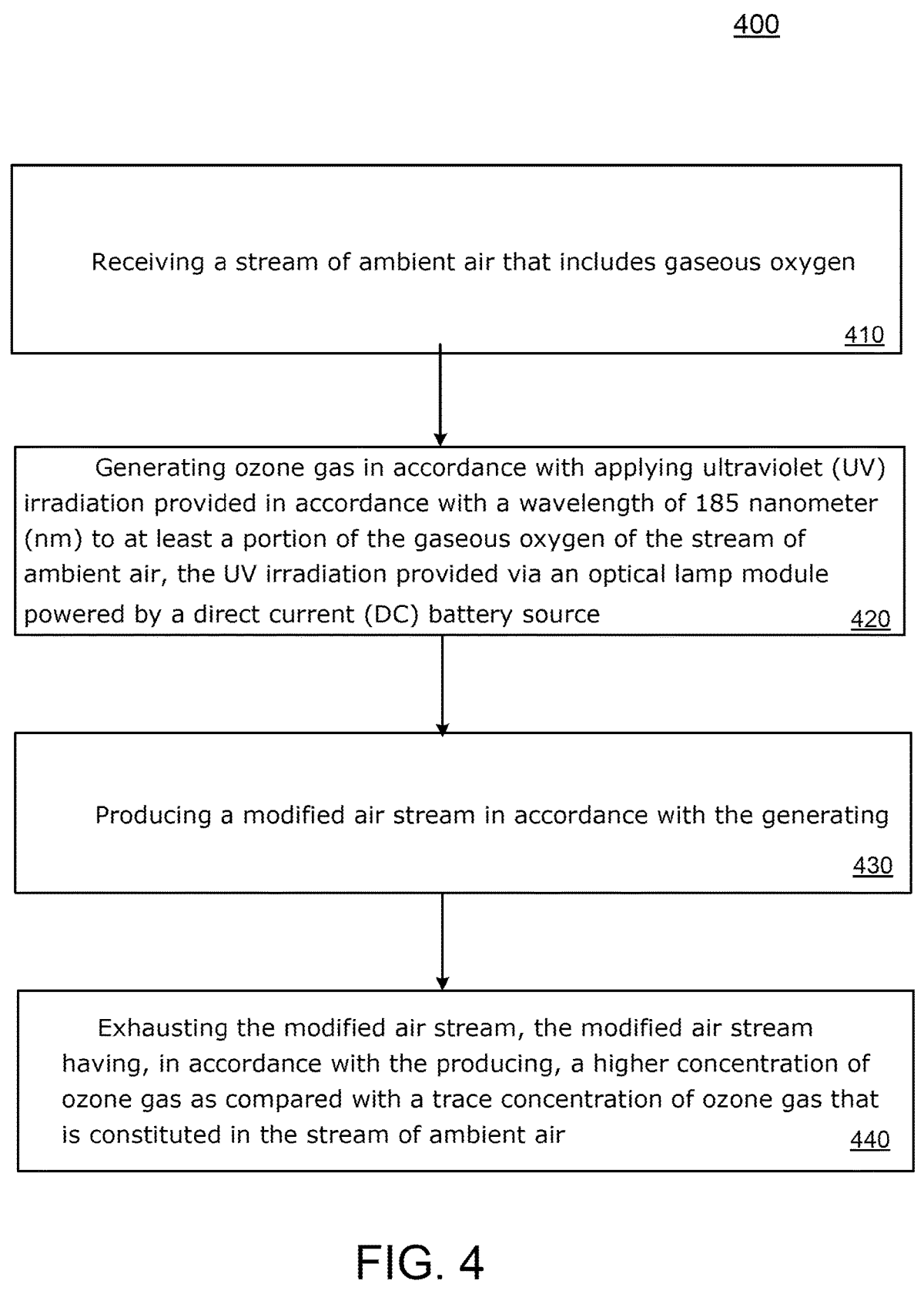

400

Receiving a stream of ambient air that includes gaseous oxygen 410

Generating ozone gas in accordance with applying ultraviolet (UV) irradiation provided in accordance with a wavelength of 185 nanometer (nm) to at least a portion of the gaseous oxygen of the stream of ambient air, the UV irradiation provided via an optical lamp module powered by a direct current (DC) battery source 420

Producing a modified air stream in accordance with the generating 430

Exhausting the modified air stream, the modified air stream having, in accordance with the producing, a higher concentration of ozone gas as compared with a trace concentration of ozone gas that is constituted in the stream of ambient air 440

Figure 7:
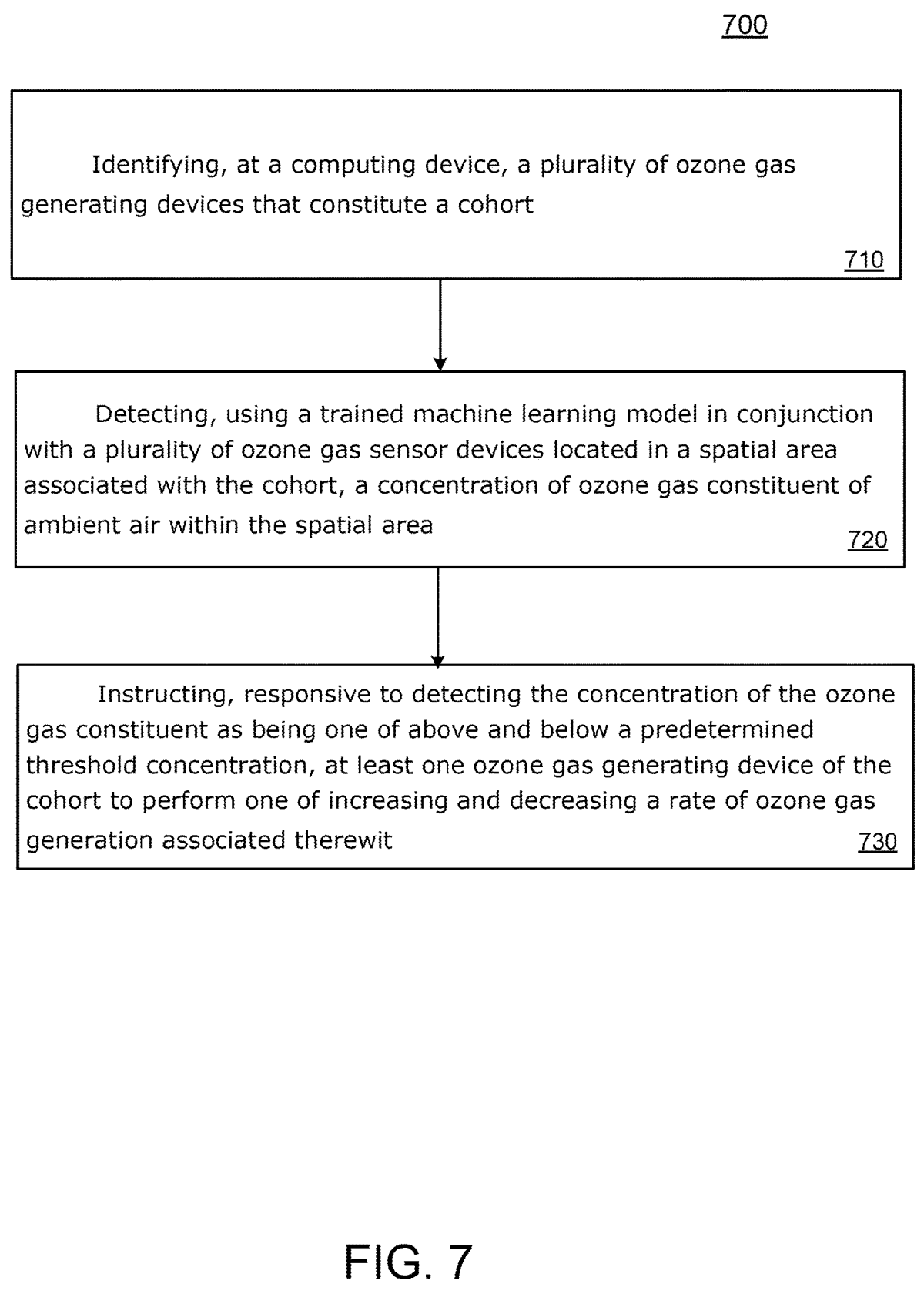

Identifying, at a computing device, a plurality of ozone gas generating devices that constitute a cohort

710

Detecting, using a trained machine learning model in conjunction with a plurality of ozone gas sensor devices located in a spatial area associated with the cohort, a concentration of ozone gas constituent of ambient air within the spatial area

720

Instructing, responsive to detecting the concentration of the ozone gas constituent as being one of above and below a predetermined threshold concentration, at least one ozone gas generating device of the cohort to perform one of increasing and decreasing a rate of ozone gas generation associated therewit

Figure 10:
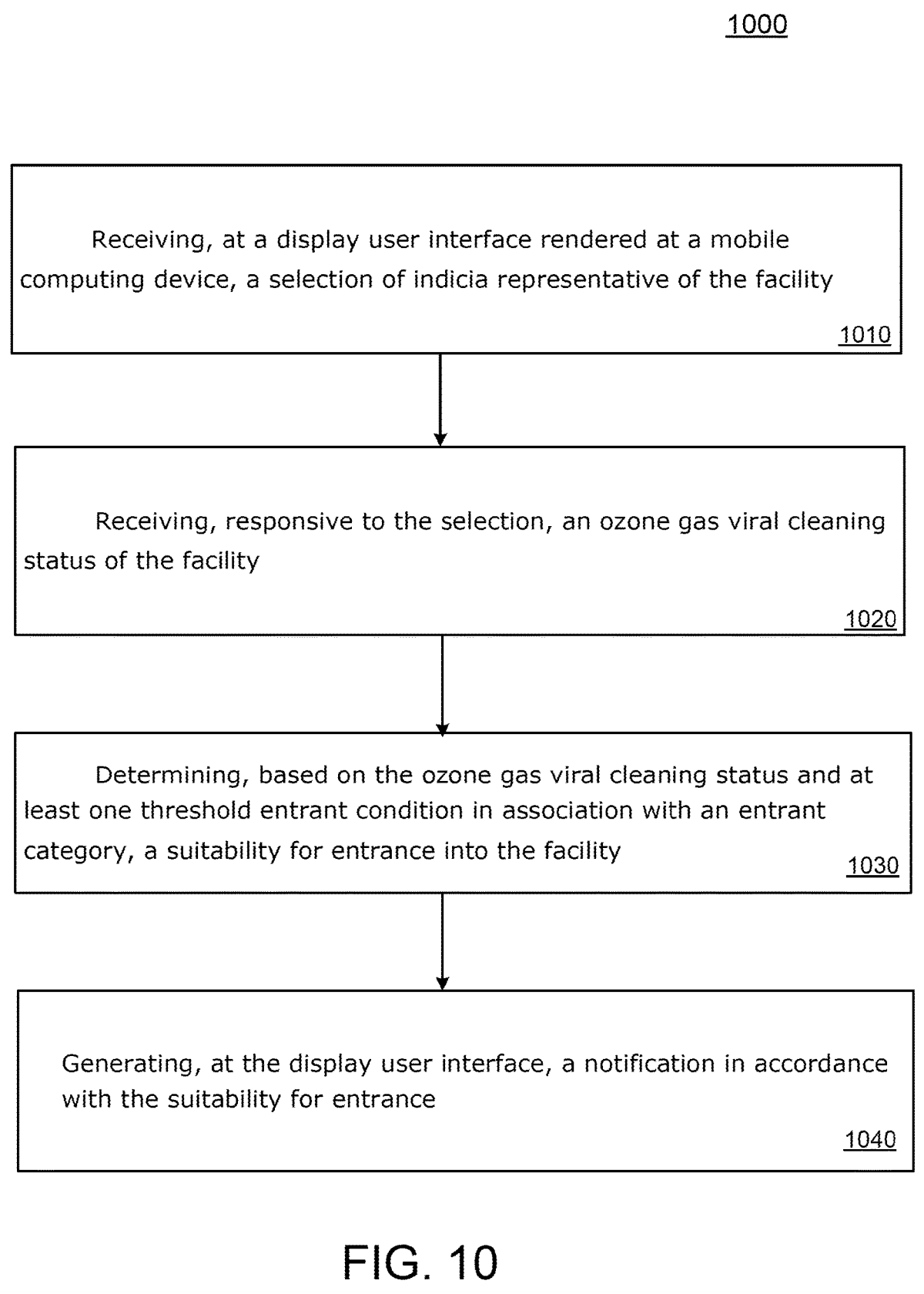

Receiving, at a display user interface rendered at a mobile computing device, a selection of indicia representative of the facility

1010

Receiving, responsive to the selection, an ozone gas viral cleaning status of the facility

1020

Determining, based on the ozone gas viral cleaning status and at least one threshold entrant condition in association with an entrant category, a suitability for entrance into the facility

1030

Generating, at the display user interface, a notification in accordance with the suitability for entrance

Notification is a prohibition against entry

Generating, at the display user interface, a request for permission to enter the facility at an earliest time of achieving suitability for entrance

1110

METHOD AND SYSTEM FOR CONFIRMATION OF VIRAL SAFETY STATUS

RELATED APPLICATIONS

This application is a continuation-in-part of, and claims the benefit of priority to, U.S. patent application Ser. No. 17/718,404, filed on Apr. 12, 2022, which in turn claims priority to U.S. patent application Ser. No. 17/699,488 filed on Mar. 21, 2022. Said U.S. patent application Ser. Nos. 17/718,404 and 17/699,488 are incorporated by reference herein.

TECHNICAL FIELD

The disclosure herein relates to monitoring and confirmation of viral safety status of facilities.

BACKGROUND

Ozone, a trace gas in the earth's atmosphere, is formed by molecules made up of 3 oxygen atoms ($O_3$) and has the characteristic of being a powerful oxidizing agent proven to be highly effective in killing bacteria, fungi and molds and inactivating viruses. Ozone can be used for the treatment of potentially contaminated surfaces, water, and ambient air thanks to its powerful germicidal effect on a wide spectrum of microorganisms. Ozone created by various kinds of ozone generators can reach every corner of the environment of a single room or a larger space, without leaving any undesired residues. The effectiveness of ozone in treating microorganisms, especially bacteria and viruses is related to various factors, such as ozone concentration, the temperature of the environment, humidity of the environment and exposure time.

BRIEF DESCRIPTION OF THE DRAWINGS

FIG. 4 illustrates, in an example embodiment, a method of operation of an ozone generating device.

FIG. 7 illustrates, in an example embodiment, a method of controlling a cohort of ozone gas generating devices that incorporates an artificial intelligence machine learning-based system.

FIG. 10 illustrates, in one embodiment, a method of confirming a viral safety status.

DETAILED DESCRIPTION

Figure 1:
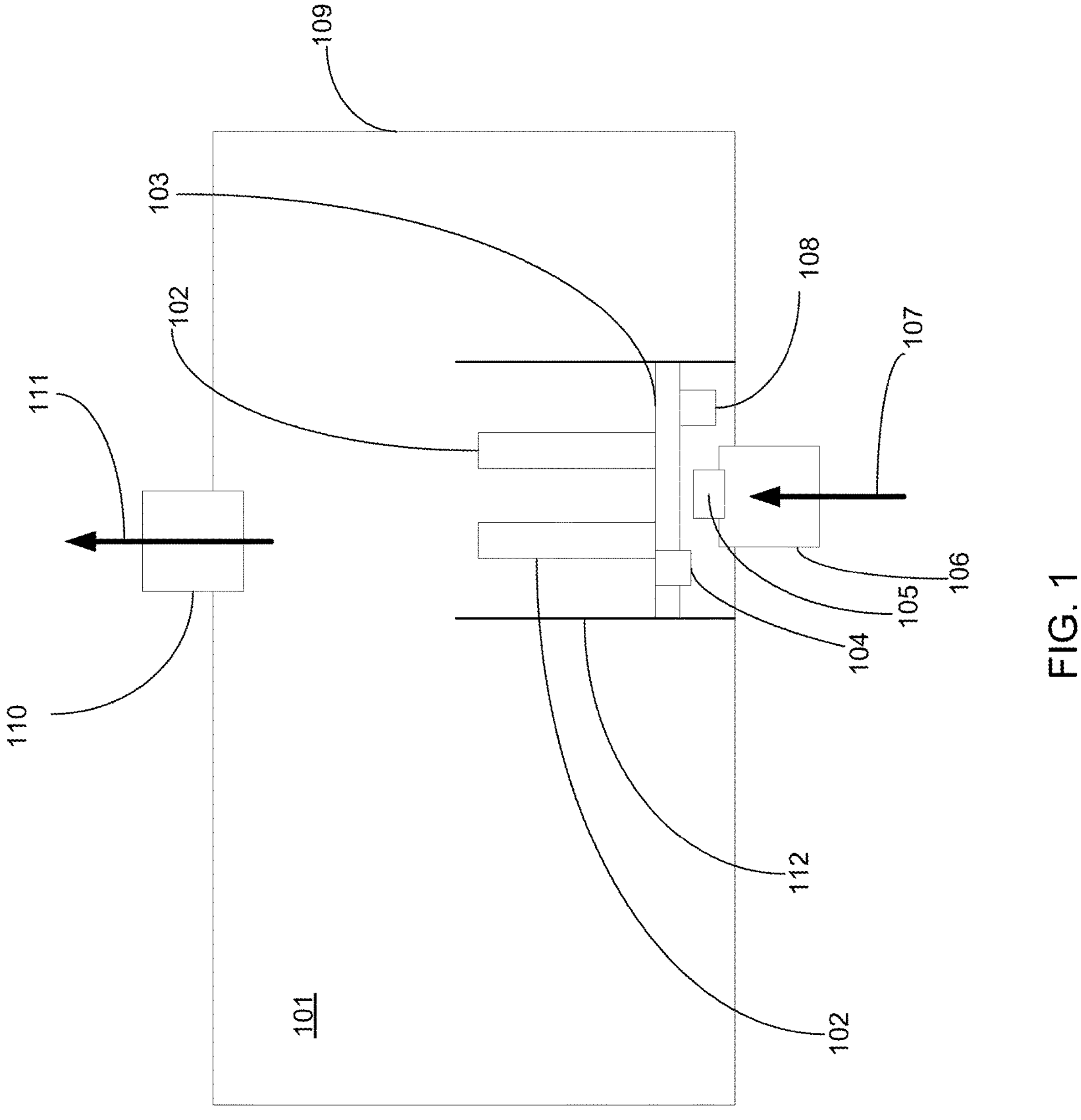
FIG. 1 illustrates, in an example embodiment, an ozone gas generating device.

Embodiments herein recognize the need for advantageously leveraging the anti-viral and anti-microbial attributes of ozone gas within an at least partially closed environment of living space, while controlling ozone gas concentration within acceptable levels in order to avoid adverse effects on human beings and other living creatures. Embodiments herein also recognize the need for ozone gas generators to operationally ramp up and swiftly attain desired ozone gas concentrations in the given living space, yet without compromising safety of any beings occupying that living space. In particular, embodiments herein provide for an ozone gas generating device capable of operating in both a regular mode of operation as well as a higher order mode of operation as characterized by increased rate of generation of ozone gas, somewhat analogous to a "turbocharged" mode of operation, but only upon ascertaining or sensing that it would be safe to do so, thus avoiding unduly high and unsafe high concentration levels that could adversely affect living beings currently occupying an at least partially enclosed room or similar living space.

Provided is a method of generating ozone gas. The method comprises receiving a stream of ambient air that includes gaseous oxygen, generating ozone gas in accordance with applying ultraviolet (UV) irradiation provided in accordance with a wavelength of 185 nanometer (nm) to at least a portion of the gaseous oxygen of the stream of ambient air, the UV irradiation provided via an optical lamp module powered by a direct current (DC) battery source, producing a modified air stream in accordance with the generating and exhausting the modified air stream, the modified air stream having, in accordance with the producing, a higher concentration of ozone gas as compared with a trace concentration of ozone gas that is constituted in the stream of ambient air. In one embodiment having a heightened safety protocol, a remote motion sensor device can be used to detect that no human persons or living creatures are active within the surroundings, such as an enclosed room in which the ozone gas generating device is located, before switching to the second mode of operation having increased rate of generation or production of ozone gas. A second modified airstream generated in this higher order, or "turbocharged", mode of operation can comprise a higher concentration of ozone gas than the first modified airstream, and optionally generated with a higher flowrate of exhausting as compared with the first modified airstream. In this manner, a higher rate of production of ozone gas can be generated within a given time period for dissemination into the surroundings safely while avoiding potentially adverse effects on living occupants in the space.

Also provided is an ozone gas generating system comprising a processor and a non-transitory memory including instructions. The instructions when executed by the processor causes the processor to perform operations comprising receiving a stream of ambient air that includes gaseous oxygen, generating ozone gas in accordance with applying ultraviolet (UV) irradiation provided in a wavelength of 185 nanometer (nm) to at least a portion of the gaseous oxygen constituted in the stream of ambient air. The UV irradiation is provided via an optical lamp module powered by a direct current (DC) battery source. Generating the ozone gas produces a modified air stream constituted of ozone-rich air which has a higher concentration of ozone gas as compared with a trace concentration of ozone gas that is constituted in the stream of ambient air and is exhausted via exhaust port 110 to the surroundings.

Embodiments herein further recognize that when multiple ones of ozone gas generating devices are portable and individually deployed in operation within a given spatial area, a need exists to ensure that the overall attendant effect, in terms of ozone gas concentration within the spatial area, is optimized for human safety while advantageously leveraging anti-viral and anti-microbial attributes. Embodiments herein further provide methods and systems for optimized control of a cohort of ozone gas generating devices using, at least in part via wireless coupling, communication with a computing device, by treating the cohort of devices in attendance at any given time as an ad hoc ozone gas generating network of devices. In this manner, individual ones of the portable ozone gas generating devices can freely join or leave the ad hoc network as their physical location transitions into, or out of, a given spatial area. In embodiments, such a network of ozone gas generating devices can be subjected to control using an artificial intelligence or machine learning neural network model, once that model is appropriately trained. In some embodiments, the control scheme can be implemented via a cloud-based server computing device, with individual ozone gas generating devices considered as respective Internet of Things (IoT) nodes within a given ad hoc network.

Further provided is a method of controlling a cohort of ozone gas generating devices. The method comprises identifying, at a computing device, a plurality of ozone gas generating devices that constitute the cohort, detecting, via at least one ozone gas sensor device located in a spatial area associated with the cohort in conjunction with one or more processors of the computing device, a concentration of ozone gas constituent of ambient air within the spatial area, and instructing, using the one or more processors responsive to detecting the concentration of the ozone gas constituent as being one of above and below a predetermined threshold concentration, at least one ozone gas generating device of the cohort to perform one of increasing and decreasing a rate of ozone gas generation associated therewith. In embodiments wherein a plurality of ozone gas sensor devices are located within the spatial area associated with the cohort, the method further includes detecting the concentration of ozone gas constituent of ambient air at least partly using a trained machine learning model in conjunction with the plurality of ozone gas sensor devices.

Also provided is a computing device, which in one embodiment may be a server computing device. The computing device includes a processor and a non-transitory memory including instructions. The instructions when executed by the processor cause the processor to perform operations comprising identifying, at a computing device, a plurality of ozone gas generating devices that constitute a cohort, detecting, via at least one ozone gas sensor device located in a spatial area associated with the cohort in conjunction with one or more processors of the computing device, a concentration of ozone gas constituent of ambient air within the spatial area, and instructing, using the one or more processors responsive to detecting the concentration of the ozone gas constituent as being one of above and below a predetermined threshold concentration, at least one ozone gas generating device of the cohort to perform one of increasing and decreasing a rate of ozone gas generation associated therewith. In embodiments wherein a plurality of ozone gas sensor devices are located within the spatial area associated with the cohort, and the instructions are further executable to detect the concentration of ozone gas constituent of ambient air at least partly using a trained machine learning model in conjunction with the plurality of ozone gas sensor devices.

Embodiments herein further recognize that a software application may be designed, installed and deployed at a mobile computing device may be used to instruct or direct prospective entrants or participants in a facility or vehicle whether it is safe, including but not limited to a viral safety perspective, to enter thereinto. In embodiments, the mobile computing device may be in communication with a server computing device that oversees and supervises ozone based anti-viral cleaning of the facility and is able to instruct prospective entrants into the facility based on communication with the server device that is monitoring and enhancing viral safety of spaces within the facility in real-time.

Provided is a method and system of monitoring viral safety status associated with entry into a facility. The method comprises receiving, at a display user interface rendered at a mobile computing device, a selection of indicia representative of the facility, receiving, responsive to the selection, an ozone gas viral cleaning status of the facility, determining, based on the ozone gas viral cleaning status and at least one threshold entrant condition in association with an entrant category, a suitability for entrance into the facility and generating, at the display user interface, a notification in accordance with the suitability for entrance.

Also provided is a mobile computing device including a processor and a non-transitory memory storing instructions, the instructions when executed by the processor causing the processor to perform operations comprising receiving, at a display user interface rendered at the mobile computing device, a selection of an indicia representative of the facility, receiving, responsive to the selection, an ozone gas viral cleaning status of the facility, determining, based on the ozone gas viral cleaning status and at least one threshold entrant condition in association with an entrant category, a suitability for entrance into the facility, and generating, at the display user interface, a notification in accordance with the suitability for entrance.

Embodiments described herein can be implemented using programmatic modules, through the use of instructions that are executable by one or more processors. A programmatic module can include a program, a sub-routine, a portion of a program, or a software component or a hardware component capable of performing one or more stated tasks or functions. As used herein, a programmatic module can exist on a hardware component independently of other modules or components, or can be a shared element of other modules, programs or machines.

One or more embodiments described herein provide that methods, techniques, and actions performed in an ozone generating device and system are performed programmatically, or as a computer-implemented method. Programmatically, as used herein, means through the use of code or computer-executable instructions. These instructions can be stored in one or more memory resources accessible to the ozone gas generating device.

FIG. 1 illustrates, in a diagrammatic representation not necessarily depicted to scale, an embodiment of ozone gas generating device 101 (variously referred to herein also as "ozone generating device 101"). In one embodiment, ozone generating device 101 includes housing 109 having ingress port 106 for ambient air stream 107 and exhaust port 110 for egress of ozone-rich air stream 111. Controller module 103 may be manifested in a printed circuit board facilitating electronic interconnection with one or more optically irradiating lamps 102 providing ultraviolet irradiation in a wavelength of 185 nanometers (nm), with direct current (DC) battery 104 providing an electrical power source and being at least partly enclosed within protective cylindrical enclosure 112. In embodiments, ozone generating device 101 operates at substantially constant-voltage as provided by DC battery 104. Local ozone gas concentration sensor 108 may be electrically interconnected to controller module 103. One or more airflow pressure differential pressure-inducing fans or similar device 105 may be deployed proximate ingress port 106 and be capable of operation in variable airflow pressure rates that induce higher or lower airflow of ambient air into ozone generating device 101 via ingress port 106, and at least partly influencing exhaust air stream 111 at correspondingly higher and lower flow rates.

Figure 2:
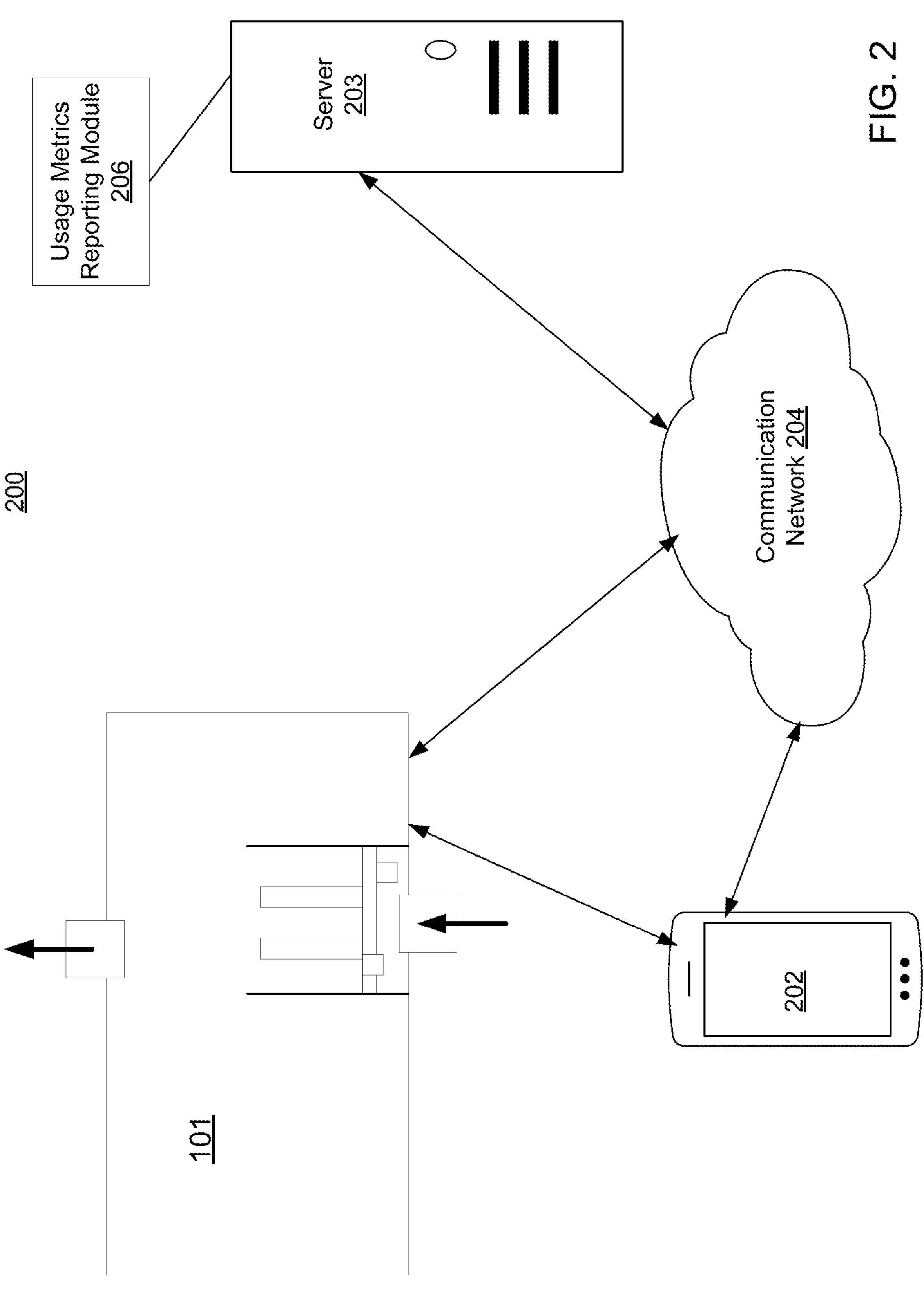
FIG. 2 illustrates, in an example embodiment, an ozone gas generating system including an ozone gas generating device.

FIG. 2 illustrates, in an example embodiment, ozone generating system 200 including ozone generating device 101. In related embodiments, it is contemplated that a group, or cohort, of ozone gas generating devices 101*a* . . . *n* (not shown) may be deployed within a given spatial area, wherein "n" is an integer number greater than 1, designating any number of additional ozone gas generating devices. Ozone generating device 101 is communicatively coupled with mobile device 202 which may be such as a mobile phone or tablet computing device. Ozone generating device 101 may also be communicatively coupled, in a cloud-based system as depicted, with server computing device 203 via communication network 204 which can, in some embodiments, be an internet or similar wide area or telecommunication-based connection. In embodiments, mobile device 202 can be communicatively linked to ozone generating device 101 via wireless communication protocols including, but not limited to, Bluetooth, Wi-Fi, LoRa or RFID. In some embodiments, mobile phone device 102 may include a software application that enables communication, either directly via wireless communication or via cloud-based system 200 via communication network 204, with ozone gas generating device 101 in order to set or apply desired threshold values or acceptable ranges of ozone gas concentration, for instance as sensed by local ozone gas concentration sensor device 108. In related embodiments, it is further contemplated that the cohort of ozone gas generating devices 101*a* . . . *n* as deployed can be communicatively coupled with corresponding ones of mobile devices 202*a* . . . *n* (not shown).

In some embodiments, usage metrics and reporting module 206 of server 203 within system 200 can acquire data, during or subsequent to a usage session, from controller module 103 of ozone generating device 101. For instance, data transmissions from controller module 103 of ozone generating device 101, can include such as, but not limited to, one or more of user or device account information, geo-location information, timestamp information, recent and accumulated historical ozone gas generation metrics during deployment, for example. In embodiments, server 203 can be maintained at a remotely located provider service or monitoring authority that is communicatively accessible via communications network 204. It is contemplated that, in some variations, at least part of the usage metrics and reporting functionality attributed to usage metrics and reporting module 206 of server computing device 203 as described herein can be deployed by way of a software application stored in a memory of mobile computing device 202 for execution thereon. In some embodiments, mobile computing device 202 can communicatively access server 203 via communication network 204.

Figure 3:
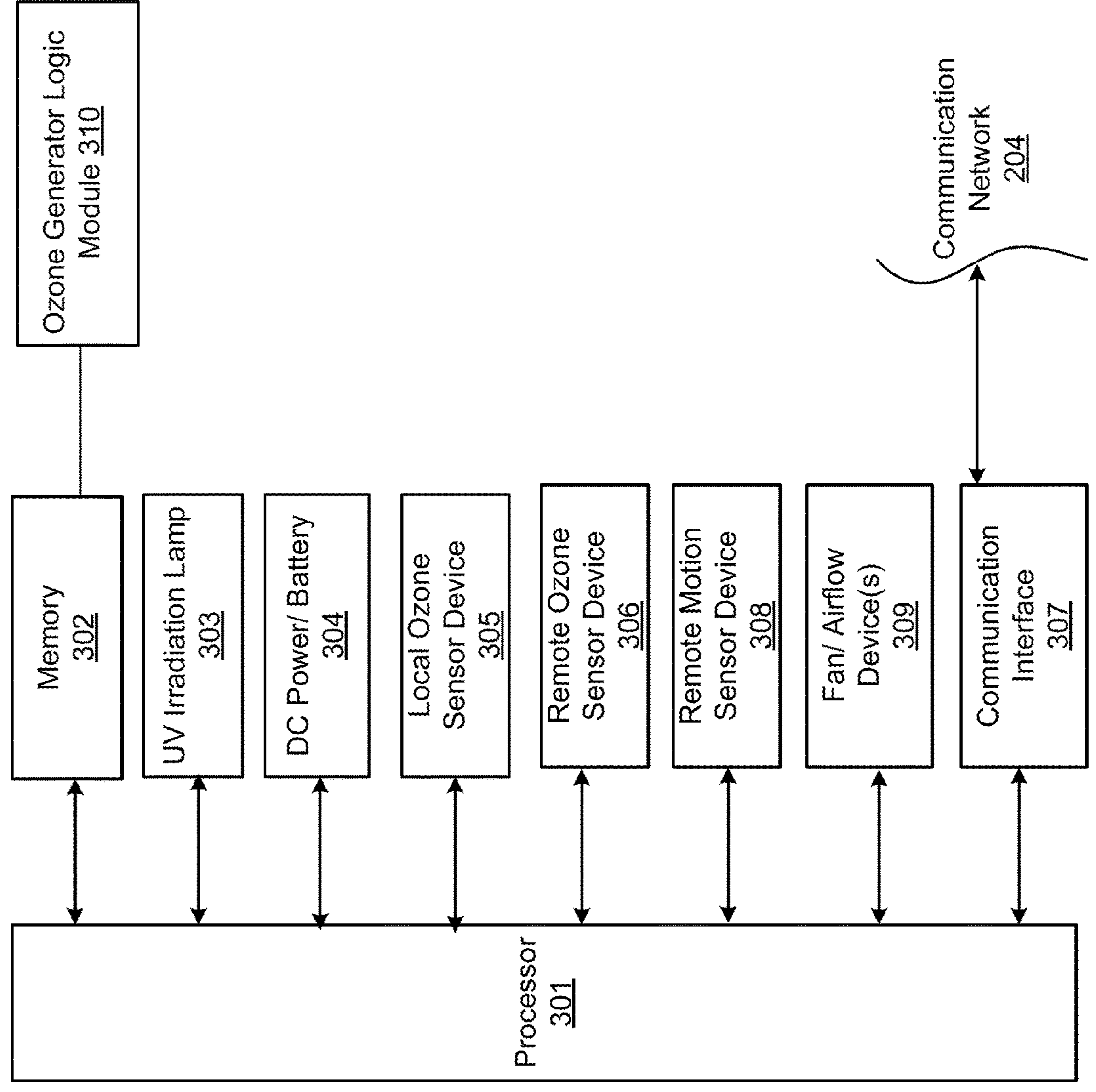
FIG. 3 illustrates, in an example embodiment, an example architecture of an ozone gas generating device deployed in an ozone generating system.

FIG. 3 illustrates, in an embodiment, example architecture 300 of controller module 103 of ozone generating device 101 as deployed within ozone generating system 200. Controller module 103, in embodiments, may include processor 301, memory 302 and be interconnected with UV irradiation lamp(s) 102, power source DC battery 304 which may be for instance a low power DC battery or similar power source operating in a range between 1.2V and 20V, and communication interface 307 that is communicatively coupled with communication network 204. Processor 301 can be implemented in an application specific integrated circuit (ASIC) device or field programmable gate array (FPGA) device, in some embodiments. Memory 302 may be such as, but not limited to, a random-access memory. Controller module 103 can also be coupled with ozone gas concentration sensor devices, including local ozone gas concentration sensor device 305 this is positioned within housing 109 and remote ozone gas concentration sensor device 305 that is positioned remotely, and external, from housing 109, such as in a room within which ozone generating device 101 is located and deployed. In embodiments, controller module 103 can also be coupled with remote motion sensor device (s) 309 to detect human presence, as inferred from motion, or lack thereof, with the area surrounding ozone generating device 101. Remote ozone gas concentration sensor devices 305 and remote motion sensor device (s) 309 may be communicatively coupled with controller module 103 via wireless communication employing Wi-Fi or similar wireless communication protocols as described herein, configured in a cloud-connected network of sensors 309, 305 with ozone gas generating devices 101*a* . . . *n* and server computing device 203. In some embodiments, the cloud connected scheme can be implemented via a cloud-based server computing device 203, with individual ozone gas generating devices 101*a* . . . *n* considered as respective Internet of Things (IoT) nodes within a given ad hoc network arranged in a mesh or a star network configuration.

Controller module 103 may also include capability for communicatively accessing wireless communication signals, including but not limited to any of Bluetooth, Wi-Fi, LoRa, RFID, and global positioning system (GPS) signals, and incorporate communication interface 307 for communicatively coupling to communication network 104, such as by sending and receiving data transmissions. Controller module 103, in some embodiments, can also incorporate GPS position location functionality based on GPS receiver and transmitter circuitry for accessing and enabling transmission of operational metrics associated with deployment of ozone generating device 101 such as, but not limited to, account information associated with ozone generating device 101, location information, timestamp information and ozone gas operational data associated with ozone generating device 101. Controller module 103 can be communicatively coupled with variable air flow generating device(s) 309, which in embodiments may be airflow pressure differential pressure-inducing fans or devices 105 as described in regard to FIG. 1.

Ozone generator logic module 310 of controller module 103, in embodiments, can be constituted of computer processor-executable code stored in memory 302 that are executable in processor 301, to accomplish ozone gas generation functionality as described herein, associated with usage or deployment of ozone generating device 101. In one embodiment, the software instructions or programs, including any updates thereof, constituting ozone generator logic module 310 can be downloaded to memory 202 by accessing and downloading, via communication network 204, from a remote server computing device, including from server 203, or from mobile computing device 202 via wireless communication protocols as described herein.

Ozone generator logic module 310 of controller module 103, in embodiments, enables deployment of ozone gas generator 101 within ozone gas generating system 200 and includes, in non-transitory memory 302, logic instructions that are executable in processor 301. The instructions when executed by processor 301 cause the processor to perform operations comprising receiving a stream of ambient air that includes gaseous oxygen, generating ozone gas in accordance with applying ultraviolet (UV) irradiation provided in a wavelength of 185 nanometer (nm) to at least a portion of the gaseous oxygen constituted in the stream of ambient air, the UV irradiation provided via an optical lamp module powered by a direct current (DC) battery source, producing a modified air stream in accordance with the generating and exhausting the modified air stream, the modified air stream having a higher concentration of ozone gas as compared with a trace concentration of ozone gas that is constituted in the incoming stream of ambient air via ingress port 106.

Ozone generator logic module 310 of controller module 103, in some embodiments, also includes, in non-transitory memory 302, logic instructions that are executable in processor 301 to adjust the rate of generating ozone gas based on local and remote sensors 305, 306, and also based on remote motion sensor 308. In embodiments, a plurality of motion sensors 308, or occupancy sensors, can be deployed within the spatial area, and being communicatively coupled to server computing device 203 and to ozone gas generating sensors 101*a* . . . *n*. In one embodiment in accordance with a heightened safety protocol, remote motion sensor device 308 can be used to detect that no human persons or living creatures are active and within the surroundings, such as an enclosed room in which the ozone gas generating device is located, before switching to a second mode of operation having increased rate of generation or production of ozone gas. In embodiments, remote motion sensor 308 may be a proximity-based sensor or may comprise similar sensors deployed to detect or infer presence or absence of living occupants within the spatial area or surroundings. For example, besides a motion sensor, ultrasonic sensors that detect shifts or changes in sound waves that might be associated with presence of living occupants may be deployed to infer presence, or absence, of living occupants within a given space around ozone gas generating device 101. Infrared radiation sensors that detect heat generated from the living occupants can also be deployed to infer presence, or absence, of living occupants within a given space around ozone gas generating device 101. Camera imaging could be deployed, in some embodiments, to detect or infer presence or absence of living occupants. A second, or alternate, modified airstream generated in this higher order, or "turbocharged", mode of operation can comprise a higher concentration of ozone gas than the first modified airstream, and optionally be generated with a higher flowrate of exhausting as compared with the first modified airstream. In this manner, under conditions where the ozone gas concentration level within a given living space is lower than a desired threshold level and no living being is active or occupying the space, a higher rate of production of ozone gas can be deployed within a given time period for safe dissemination into the surroundings while avoiding potentially adverse effects on living occupants in the space. In embodiments, a safe and desired threshold level of ozone gas concentration that provides effective anti-viral and anti-bacterial functions, as sensed by either local ozone gas sensor device 305 or remote ozone gas sensor device 306, may be in the range between 50 parts per billion (ppb) and 100 ppb, though it is contemplated that other ranges or values can be implemented.

In some embodiments, when the higher order or "turbocharged" mode is being deployed, one or more of ozone gas generating devices 101*a* . . . *n*, or server computing device 203, may initiate a warning or alert, that it would be unsafe for an individual to enter the spatial area. For example, in an embodiment where the spatial area is a hotel room, flashing LED alert lights may warn an incomer attempting to enter the room that it would be unsafe to enter the room. In some variations, the warning could further advance to initiate a lockout state of the hotel room via existing door locks, to where an incomer would not be able to enter the room or similar enclosed area while one or more of ozone gas generating devices 101*a* . . . *n* are operating in the "turbocharged" mode. Associated with the warning or alert, which in one embodiment, may be a "cleaning in progress—do not enter" message displayed to the incomer attempting to enter the room. In related embodiments, the warning or alert could also include a smoke alarm or piezo-based buzzer already deployed within the hotel room, via existing wireless communication, including via WiFi connectivity. In additional embodiments, a cloud-based alarm system, including but not limited to a smoke or fire alarm) may be triggered by the server computing device 203, if an unsafe ozone condition higher than a threshold ozone gas concentration, is detected.

FIG. 4 illustrates, in an example embodiment, method of operation 400 of ozone generating device 101. Examples of method steps described herein are related to deployment and use of ozone generating device 101 as described herein. According to one embodiment, the techniques are performed in processor 301 executing one or more sequences of software logic instructions that constitute ozone generator logic module 310 of controller module 103. In embodiments, instructions constituting ozone generator logic module 310 may be read into memory 302 from machine-readable medium, such as memory storage devices. Executing the instructions of ozone generator logic module 310 stored in memory 302 causes processor 301 to perform the process steps described herein. In alternative implementations, at least some hard-wired circuitry may be used in place of, or in combination with, the software logic instructions to implement examples described herein. Thus, the examples described herein are not limited to any particular combination of hardware circuitry and software instructions.

At step 410, receiving a stream of ambient air that includes gaseous oxygen via an ingress port within a housing of an ozone generating device.

At step 420, generating ozone gas in accordance with applying ultraviolet (UV) irradiation provided in a wavelength of 185 nanometer (nm) to at least a portion of the gaseous oxygen of the stream of ambient air, the UV irradiation provided via an optical lamp module powered by a direct current (DC) battery source. The shorter 185 nanometers wavelength of UV irradiation generates ozone by reacting with oxygen in the ambient air stream to break it into atomic oxygen, making available a highly unstable oxygen atom that then combines with oxygen in the ambient air stream to form ozone.

At step 430, producing a modified air stream in accordance with the generating. In some embodiments, either one of local ozone gas sensor device 305 or remote ozone gas sensor device 306 can sense ozone concentration being produced by ozone generator device 101, and if the sensed ozone gas concentration level is higher than a predetermined threshold level, processor 301 can operate optical lamp module 102 using an intermittent, duty cycle-based, on/off powered pattern that moderates ozone gas generation into a more acceptable range, and then to maintain it within that range. In some example embodiments, between 50-500 ppb may be predetermined as such an acceptable range, though other ppb values may be deployed. In embodiments, the threshold levels deemed acceptable can be set, or changed from a pre-existing value or values via mobile phone device 202.

At step 440, exhausting the modified air stream via an exhaust port of the housing, the modified air stream having a higher concentration of ozone gas as compared with a trace concentration of ozone gas that is constituted in the stream of ambient air.

In yet another variation, the method can include transmitting, to a computing device such as a remote server computing device, one or more of account information, location information and timestamp information associated with ozone generator device 101 and details of its operation within ozone gas generating system 200.

Figure 5:
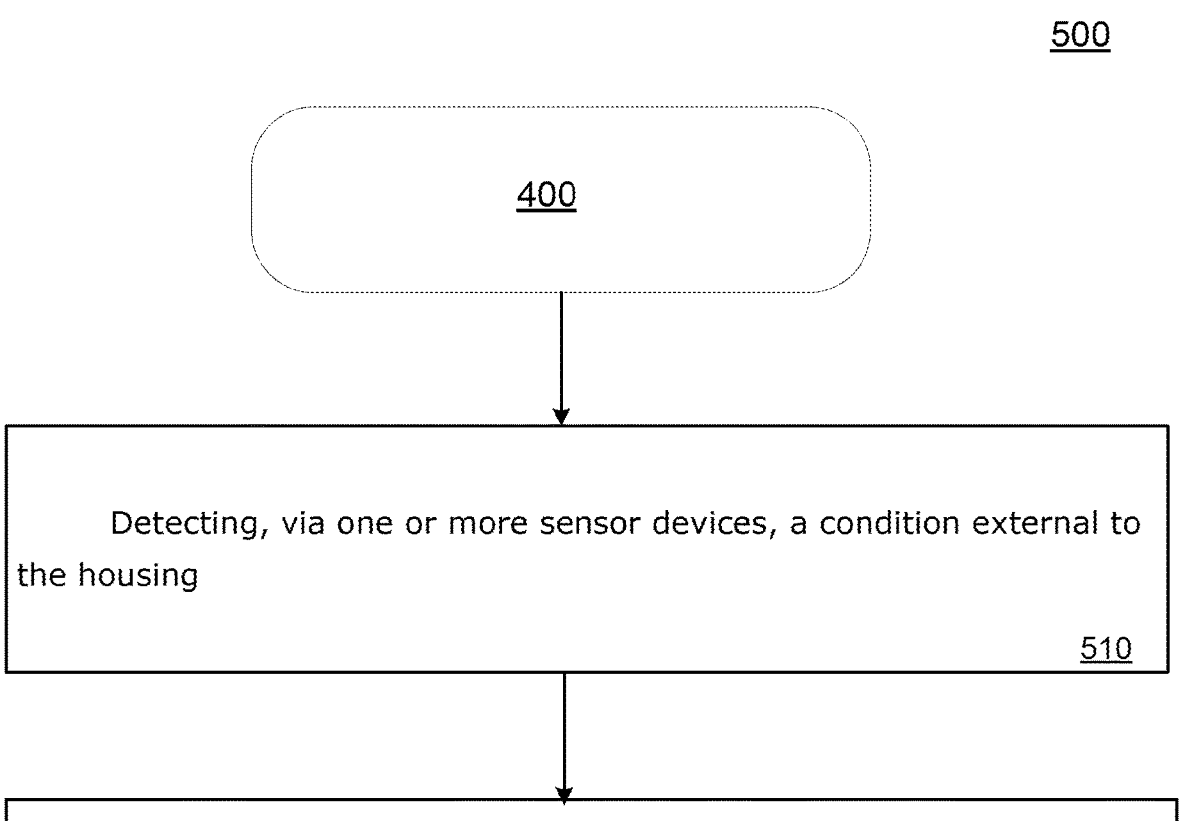
FIG. 5 illustrates, in yet another example embodiment, a method of operation of an ozone generating device in accordance with a higher order method of operation.

FIG. 5 illustrates, in yet another example embodiment, a further method of operation 500 of ozone generating device 101. In one embodiment in accordance with a heightened safety protocol, remote motion sensor device 308 can be used to detect that no human persons or living creatures are active and within the surroundings, such as an enclosed room in which the ozone gas generating device is located, before switching to a second mode of operation having increased rate of generation or production of ozone gas. A second, or alternate, modified airstream generated in this higher order, or "turbocharged", mode of operation can comprise a higher concentration of ozone gas than the first modified airstream, and optionally be generated with a higher flowrate of exhausting as compared with the first modified airstream. In this manner, under conditions where the ozone gas concentration level within a given living space is lower than a desired threshold level and no living being is active or occupying the space as determined in accordance with remote motion sensor device 308, a higher rate of production of ozone gas can be deployed within a given time period for safe dissemination into the surroundings while avoiding potentially adverse effects on living occupants in the space. In embodiments, a safe and desired threshold level of ozone gas concentration that provides effective anti-viral and anti-bacterial functions, as sensed by either local ozone gas sensor device 305 or remote ozone gas sensor device 306, may be in the range between 5 parts per billion (ppb) and 1,000 ppb. However, it is contemplated that other ranges or values can be deployed; for instance, in a range from 50 ppb to 500 ppb of ozone gas concentration.

At step 510, detecting, via one or more remote sensor devices 306, a condition that is external to the housing. In one embodiment, the condition external to the housing can be determined as being an absence of a person within a predetermined area around the housing, using one or more remote motion sensor device(s) 308.

In a further variation, using one or more remote ozone gas concentration sensor device(s) 306, the condition external to the housing can be determined as a concentration of ozone gas being below a predetermined threshold concentration, for instance in a range of 50 to 500 ppb, within a predetermined area around the housing of ozone gas generating device 101.

At step 520, switching, responsive to the detecting, to a second mode of operation that produces a second modified airstream, the second modified airstream comprising at least one of: (i) a higher concentration of ozone gas than the first modified airstream, and (ii) a higher flowrate of the exhausting as compared with the first modified airstream. In this manner, a higher rate of production of ozone gas can be generated within a given time period and subsequently disseminated into the surroundings. In one embodiment having a heightened safety protocol, remote motion sensor device 308 can be used to detect that no human person(s) are active or occupying the surroundings, such as an enclosed room in which gas generating device 101 is located, before switching to the second mode of operation having increased rate of generation or production of ozone gas.

In an embodiment, the optical lamp module includes one or more optical lamps, and the second mode of operation comprises activating at least one additional optical lamp of the optical lamp module.

In another variation, the higher flowrate of the second modified air stream is accomplished in accordance with varying an operational state of one or more pressure differential-inducing devices disposed at least partially within the housing. Such varying of operational state can be accomplished by activating additional fans, speeding up deployed fans, or any combination thereof, whereupon additional fans and/or fans operating at higher speeds accomplish higher ozone generation rates, and faster times to reach a given concentration of ozone gas, in accordance with the higher order, or "turbocharged", mode as described herein.

In yet another embodiment, the method includes terminating at least the second mode of operation, responsive to detecting that a concentration of ozone gas exceeds a predetermined threshold concentration in ppb in an area around the housing.

Figure 6:
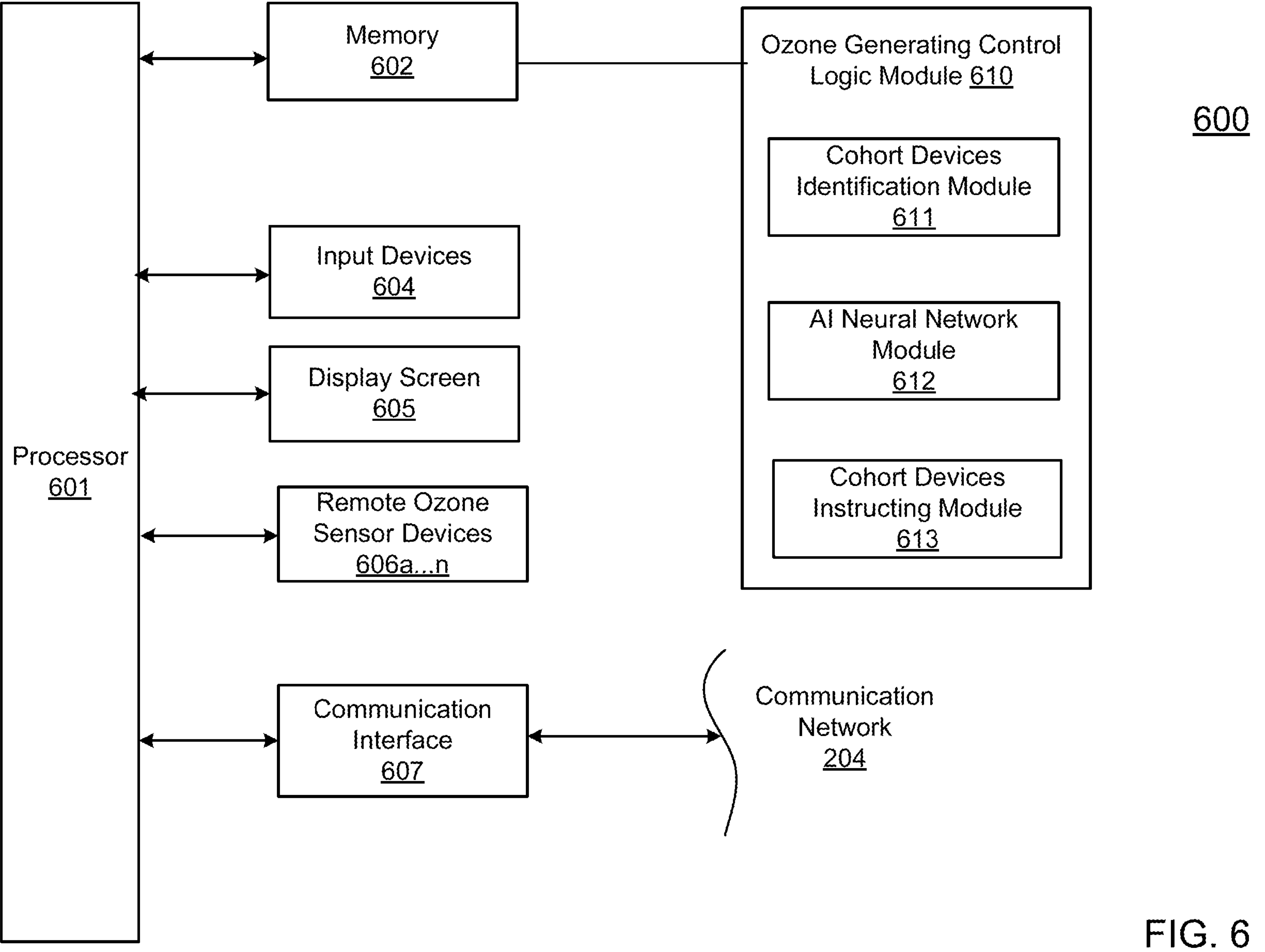
FIG. 6 illustrates, in an example embodiment, a computing device architecture incorporating an artificial intelligence machine learning-based system for controlling a cohort of ozone gas generating devices.

FIG. 6 illustrates, in an example embodiment, computing device architecture 600 incorporating an artificial intelligence machine learning-based system for controlling a cohort of ozone gas generating devices 101*a* . . . *n*. The term cohort, as referred to herein, refers to a group of ozone gas generating devices deployed within a given spatial area for the common, or individual, purpose of generating ozone gas within ambient air of that spatial area. The spatial area may be a room, a hall, an enclosed or partially enclosed area, and can defined in terms of location coordinates, either in local or global (x,y) coordinates that define a boundary or perimeter enclosing the spatial area.

Server computing device 203, in a cloud-based embodiment, includes processor 601, memory 602, display screen 603, input mechanisms 604 such as a keyboard or software-implemented touchscreen input functionality, and communication interface 607 for communicating via communication network 204. Remote ozone sensor devices 606*a* . . . *n* are physically located in the spatial area associated with the cohort of ozone gas generating devices 101*a* . . . *n*, but are communicatively interfaced with processor 601 of server computing device 203 via wireless communication using communication network 204 and communication interface 607. Memory 602 may comprise any type of non-transitory system memory, storing instructions that are executable in processor 601, including such as a static random access memory (SRAM), dynamic random access memory (DRAM), synchronous DRAM (SDRAM), read-only memory (ROM), or any combination thereof.

Ozone generating control logic module 610 includes processor-executable instructions stored in memory 602 of server computing device 203 in a cloud-based embodiment, the instructions being executable in processor 601. Neural network logic module 105 may comprise portions or sub-modules including cohort devices identification module 611, artificial intelligence (AI) neural network module 612, and cohort devices instructing module 613.

Processor 201 uses executable instructions stored in cohort devices identification module 611 to identify, at server computing device 203 in one embodiment, a plurality of ozone gas generating devices 101*a* . . . *n* that constitute the cohort. Ones of ozone gas generating devices 101*a* . . . *n* that are in operation within a given spatial area may be classified, or assigned, as belonging to a cohort based on their physical locations as sensed by server computing device 203. The spatial area may be designated in accordance with coordinate (x,y) locations or perimeter that is predetermined, such as a room, a hall or similar area. Physical locations of respective ozone gas generating devices 101*a* . . . *n* can be determined or estimated using global positioning system in conjunction with a GPS receiver in the ozone generating devices 101*a* . . . *n*, or also estimated as a location corresponding with a respective one of mobile phones 202*a* . . . *n* in wireless communication therewith. In some embodiments, ozone gas generating devices 101*a* . . . *n* can be in wireless communication, such as but limited to Bluetooth protocol, with a fixed wireless communication access point device within the spatial area, with coordinate (x,y) locations within the spatial area being estimated based on received wireless signal strengths.

Processor 201 uses executable instructions stored in AI, or machine learning, neural network module 612 to detect, via at least one of ozone gas sensor devices 606*a* . . . *n* located in a spatial area associated with the cohort in conjunction with one or more processors of computing device 203, a concentration of ozone gas constituent of ambient air within the spatial area. In embodiments, the concentration of ozone gas constituent of ambient air may be detected based on at least partly upon using a trained machine learning model in conjunction with the plurality of ozone gas sensor devices 606*a* . . . *n*.

FIG. 7 illustrates, in an example embodiment, method 700 of controlling a cohort of ozone gas generating devices 101*a* . . . *n* that incorporates an artificial intelligence machine learning neural network-based system.

At step 710, identifying, at computing device 203, a plurality of ozone gas generating devices 101*a* . . . *n* that constitute the cohort.

At step 720, detecting, via at least one of remote ozone gas sensor devices 606*a* . . . *n* located in a spatial area associated with the cohort in conjunction with one or more processors 601 of the computing device 203, a concentration of ozone gas constituent of ambient air within the spatial area.

At step 730, instructing, using the one or more processors 601 responsive to detecting the concentration of the ozone gas constituent as being one of above and below a predetermined threshold concentration, at least one ozone gas generating device of the cohort 101*a* . . . *n* to perform one of increasing and decreasing a rate of ozone gas generation associated therewith.

In embodiments, the at least one remote ozone gas sensor device comprises a plurality of remote ozone gas sensor devices 606*a* . . . *n* located within the spatial area associated with the cohort, but not necessarily incorporated within ozone gas generating devices 101*a* . . . *n* as distinct from local ozone gas concentration sensors 108, and the method further comprises detecting the concentration of ozone gas constituent of ambient air at least partly using a trained machine learning model in conjunction with plurality of ozone gas sensor devices 606*a* . . . *n*. In one aspect, the trained machine learning model comprises one of a trained convolutional neural network and a trained recurrent neural network.

In one variation, responsive to the instructing, the at least one ozone gas generating device of the cohort 101*a* . . . *n* increases the rate of ozone gas generation associated therewith in accordance with switching from a first mode to a second mode of ozone gas generation, the second mode of ozone gas generation being associated with a higher rate of generation of ozone gas than the first mode.

In one aspect, the at least ozone generating device includes an optical lamp module comprised of a plurality of optical lamps 102, and the second mode of ozone gas generation comprises activating at least one additional optical lamp of the plurality of optical lamps 102.

In yet another aspect, responsive to the instructing, the at least one ozone gas generating device of the cohort 101*a* . . . *n* decreases the rate of ozone gas generation associated therewith in accordance with ay least one of (i) switching from the second mode to the first mode of ozone gas generation, and (ii) switching from an operational state to a non-operational state, where the operational state refers to a state of active generation of ozone gas, and the non-operational state may be a power-off or inactive state where no ozone gas is being generated.

In yet another embodiment, the at least one ozone generating device includes an optical lamp module comprised of a plurality of optical lamps 102, and the first mode of ozone gas generation comprises de-activating at least one optical lamp of the plurality of optical lamps 102.

Figure 8:
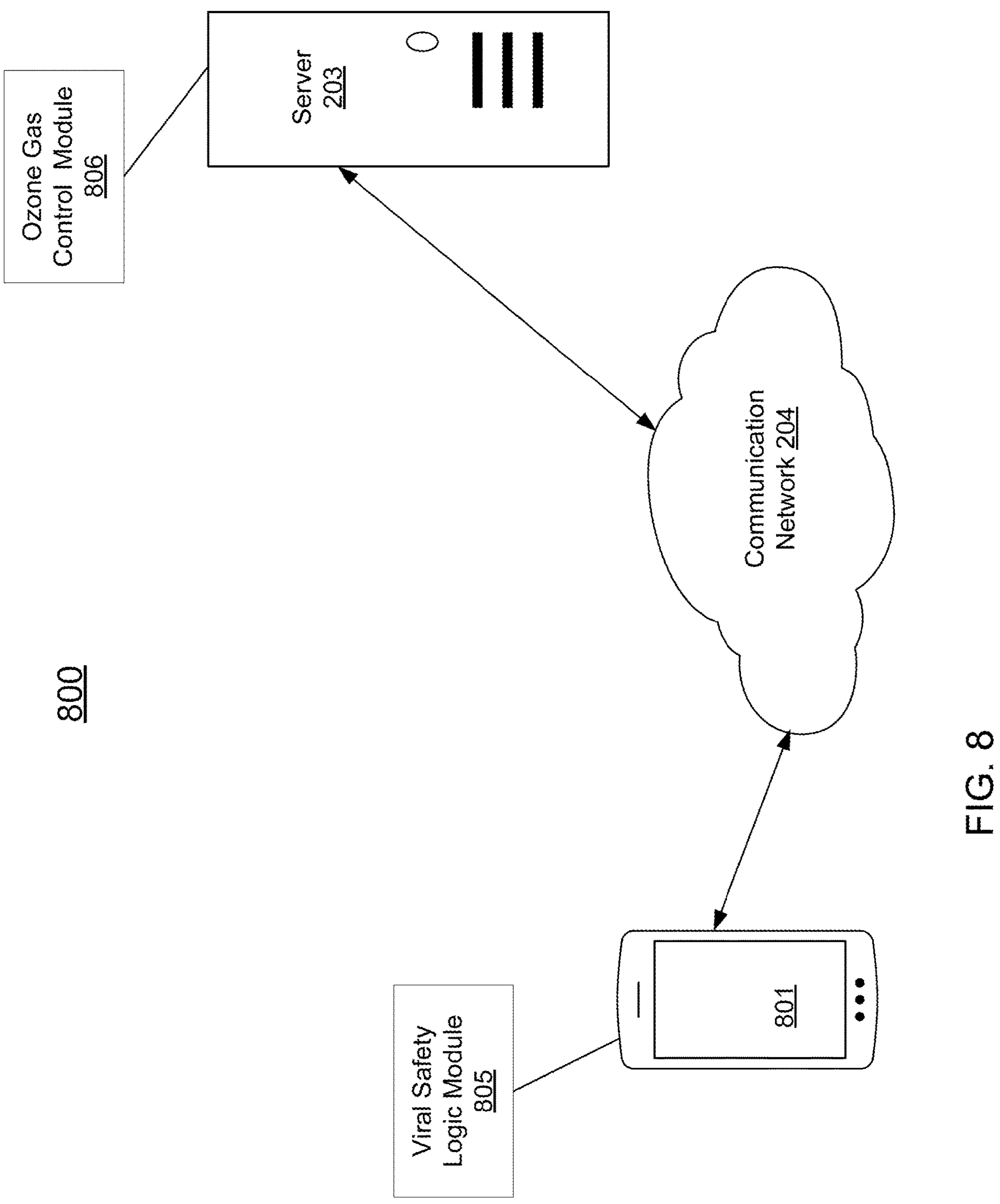
FIG. 8 illustrates, in an example embodiment, a system for confirming a viral safety status.

FIG. 8 illustrates, in an example embodiment, system 800 for confirming a viral safety status. Mobile computing device 801, which may be such as a mobile phone device, a tablet computing device or a laptop computing device, is communicatively connected with server 203 via communication network 204. Mobile computing device 801 includes, in a non-transitory memory, viral safety logic module 805 that is constituted of processor-executable instructions. Viral safety logic module 805, in some embodiments, can be a downloadable software application. In one embodiment, viral safety logic module 805 can be downloaded from cloud-based server 203 via communication network 204. Server 203, as described herein with reference to one of more of FIGS. 1-7, includes capability for monitoring and controlling ozone gas generation, in real-time, within a facility for anti-viral cleaning purposes, such facility being considered for entry thereinto, or human occupancy, by a user of mobile computing device 801.

Figure 9:
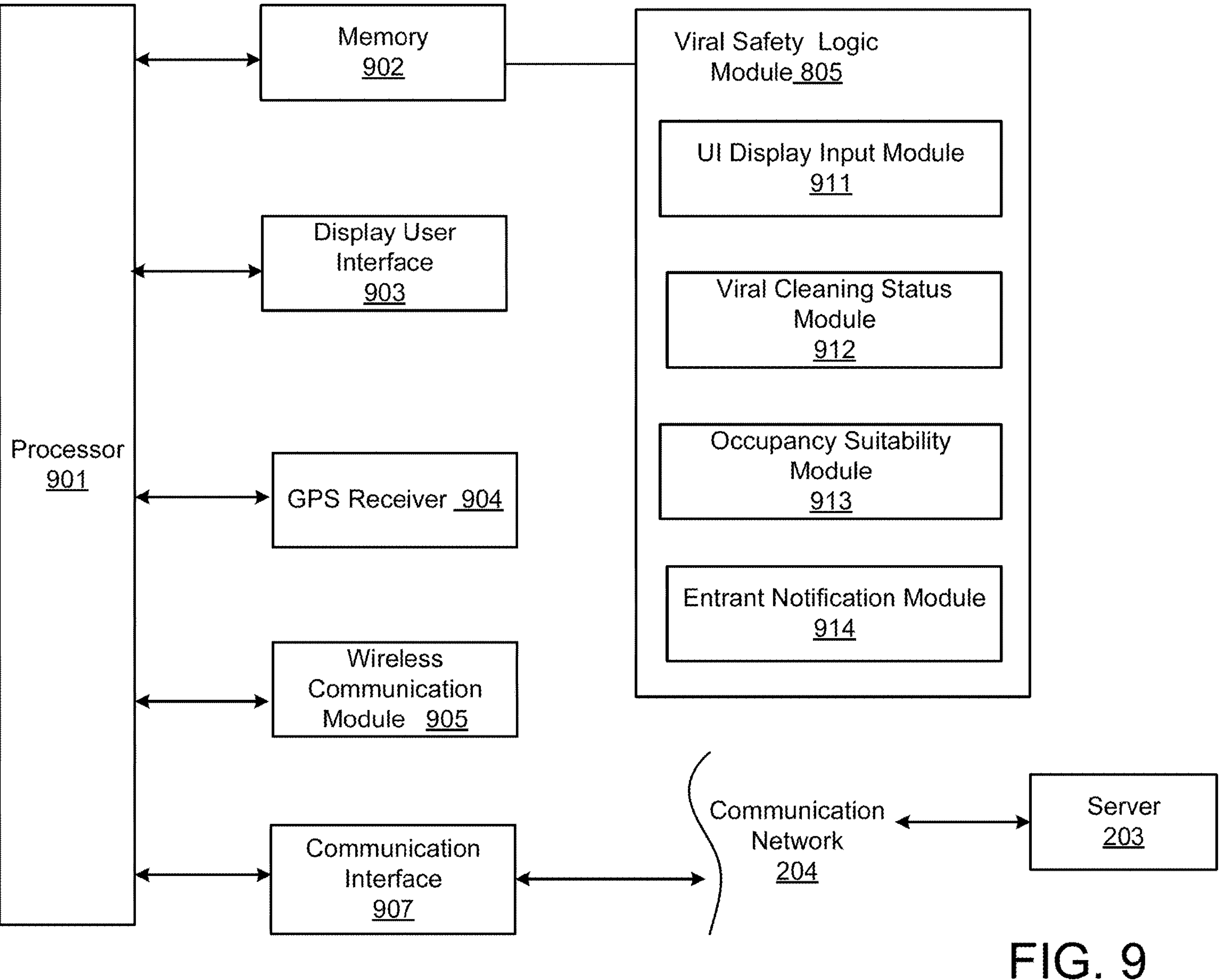
FIG. 9 illustrates, in one embodiment, a mobile computing device architecture for deployment in confirming a viral safety status.

FIG. 9 illustrates, in one embodiment, an architecture 900 of mobile computing device 801 for deployment in confirming a viral safety status within a given facility. In some embodiments, mobile computing device 801 incorporates one or more features as described herein with regard to mobile computing device 202. Mobile computing device 801 includes processor 901, non-transitory memory 902 storing processor-executable instructions of viral safety logic module 805, and user input capability, including, but not limited to, user input by touch screen user interface display 903. Mobile computing device 801 includes global positioning system (GPS) receiver circuitry in deployment of location-awareness functionality, and also incorporates inertial navigation capability by way of various sensor devices, including, but not limited to, accelerometer, gyroscope and magnetic compass sensor devices. Mobile computing device 801 also includes wireless communication module 905 in accordance with various wireless communication protocols, including, but not limited to, Wi-Fi and Bluetooth wireless communication protocols. Mobile computing device 801 also includes communication interface 907 for communicative access with server 203 via communication network 204. Viral safety logic module 805 includes processor-executable instructions constituting submodules user interface (UI) display input module 911, viral cleaning status module 912, occupancy suitability module 913 and entrant notification module 914.

User interface (UI) display input module 911 includes processor-executable instructions to receive, at display user interface 903 rendered at mobile computing device 801, a selection of indicia representative of the facility. As referred to herein, the term facility as used herein is intended to mean any place, amenity, or piece of equipment, provided for a particular purpose, and include not only buildings fixed in place, but also mobile buildings and machinery, including transportation machinery and equipment.

Viral cleaning status module 912 includes processor-executable instructions to receive, responsive to the selection made at display user interface 903 rendered at mobile computing device 801, an ozone gas viral cleaning status of the facility as transmitted from server 203.

Occupancy suitability module 913 includes processor-executable instructions to determine, based on the ozone gas viral cleaning status and at least one threshold entrant condition in association with an entrant category, a suitability for entrance into the facility. "Entrant category" as used herein refers to different classes on prospective entrants to the facility, such as adults versus children versus pets, in embodiments, and could apply to any category of prospective entrants—humans wearing protective gear, wearing no protective gear, children, animals, etc. It is contemplated that other entrant categories or classes could be used, based on each entrant category having respectively different tolerances for prevailing ozone gas concentration during the anti-viral cleaning process underway in the facility. In some embodiments, the suitability for entrance may be predetermined as a range defined by an upper threshold limit and a lower threshold limit of ozone gas ppb concentration, including an upper threshold of 500 ppb and a lower threshold of 50 ppb concentration, though other ranges are contemplated as well. In embodiments, the facility comprises one of an at least partially enclosed building, a mobile facility, a vehicle, and a transportation machinery, the viral safety status associated with entry comprises one or more of: a time period prior to an attempted entry into the facility, a time period upon entry into the facility and a time period while within the facility, and the ozone gas viral cleaning status of the facility comprises an ozone gas concentration level within the facility. Different entrant categories may include an adult person, a child, a person attired in protective gear, and an animal.

Entrant notification module 914 includes processor-executable instructions to generate, at the display user interface 903, a notification in accordance with the suitability for entrance. In embodiments, the suitability for entrance in accordance with a range of ozone gas concentration as defined by an upper and a lower threshold limits of ozone gas concentration. In some embodiments, mobile computing device 801 may capture and allow display of recent trend in viral safety vs the applicable threshold for a given entrant class depending on trending/cleaning in progress for a given facility. It is also contemplated that viral safety logic module 805 of mobile computing device 801 may project, from trends in most recent cleaning information in conjunction with cleaning in progress, as to when the facility might be safe to enter, and appropriately notify respective categories of prospective entrants in turn. In an embodiment, the upper threshold limit is 500 parts per billion (ppb) and the lower threshold limit is 50 ppb of ozone gas concentration.

In embodiments, the notification comprises, in conjunction with identification of at least one entrant category, one of: a permission to enter, a prohibition against entry, and an estimated time period prior to receiving permission to enter the facility. In one aspect, the prohibition against entry includes confirmation of an entrance lockout state being initiated and the estimated time period prior to receiving permission relates to termination of the entrance lockout state.

FIG. 10 illustrates, in one embodiment, a method 1000 of confirming a viral safety status. In regard to method 1000 being described via enactment at mobile computing device 801, it is contemplated that, in alternatives, one or steps, including portions thereof as described may be capable of being enacted via server 203 which is in network communication mobile computing device 802.

At step 1010, receiving, at a display user interface 903 rendered at a mobile computing device 801, a selection of indicia representative of the facility. The indicia may be selectable icon identifying the facility of interest for entering based on an address, building name or map location, among other possibilities. In some embodiments, mobile computing device 801 can include location-aware functionality and indicate the facility of interest in a map location display. Mobile computing device 801 can include location-aware functionality and determine estimated time of arrival at the facility entrance as projected from a current location of the user of mobile computing device 801 in accordance with its location-aware capability.

At step 1020, receiving, responsive to the selection made at display user interface 903 rendered at a mobile computing device 801, an ozone gas viral cleaning status of the facility, in one embodiment as transmitted from control server 203 thereto.

At step 1030, determining, based on the ozone gas viral cleaning status and at least one threshold entrant condition in association with an entrant category, a suitability for entrance into the facility.

At step 1040, generating, at the display user interface 903 of mobile computing device 801, a notification in accordance with the suitability for entrance.

Figure 11:
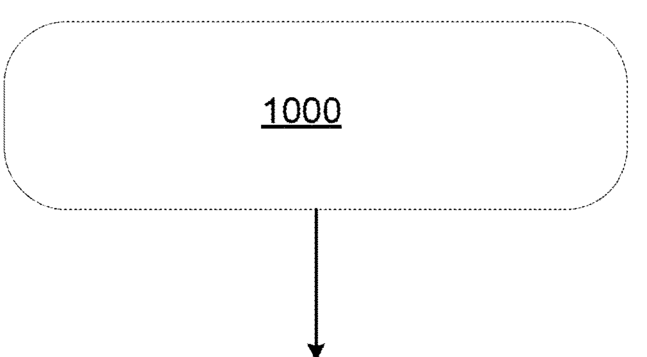
FIG. 11 illustrates, in one embodiment, a further method of confirming a viral safety status.

FIG. 11 illustrates, in one embodiment, a further method of confirming a viral safety status.

At step 1110, based on the notification generated at display user interface 903 being a prohibition against entry, such as a "DO NOT ENTER" directive, the method, in another variation, can further include inviting, of the user at the display user interface 903 of mobile computing device 801, a request for permission to enter the facility at an earliest time of achieving suitability for entrance. Based on such a request generated at mobile device 801, ozone gas cleaning control server 203 (also referred to as server 203 herein) can infer that a prospective entrant is awaiting entry, and based on authenticating that person or persons, may take steps to enhance the rate of ozone gas generation and ozone gas generation within the facility in order to accommodate the waiting parties. The enhanced rate of cleaning may be set in motion by ozone gas cleaning control server 203 initiating techniques as described herein, for example, ozone gas cleaning control server 203 may trigger the "turbo" mode of ozone gas generation for higher order or accelerated ozone gas anti-viral cleaning, intended to shorten waiting times of permitted persons before they can enter the facility. In some embodiments, control server 203 may defer anti-viral cleaning in the turbocharged mode if other persons are already occupying the space within the facility as it may not be safe if doing would risk subjecting them to higher ozone gas concentration rates than would be advisable.

In related embodiments, techniques of confirming a safety as described herein, or some aspects thereof, may be deployed based on aggregating sensor data gather from cloud-based internet of things (IoT) sensors, not necessarily limited to only ozone sensor devices. Yet further, it is contemplated that such sensor data can be combined with information from other sources or databases in a cloud-based arrangement, to create a rich safety-related map of a person's environment and its prevailing or potential safety conditions as that person traverses along routes or travels to particular geo-localities. In this manner of deployment via a mobile computing device interface as described herein, a person can be enabled to make the optimum choices in whether to enter certain areas, travel along routes or enter certain infrastructures and mobile vehicles or equipment. In some embodiments, the data acquired from such sensor devices can include, but not necessarily be limited to, carbon monoxide, sulphur dioxide, nitrogen dioxide, particulates including PM2.5 and PM10, air quality index (AQI), temperature and humidity sensor devices, and used to confirm a related safety status in conjunction with information from data sources and databases that are communicatively accessible via a mobile computing device being carried by a person.

Although embodiments are described in detail herein with reference to the accompanying drawings, it is contemplated that the disclosure herein is not limited to only such literal embodiments. As such, many modifications including variations in sequence of the method steps in conjunction with varying combinations of user interface features disclosed herein will be apparent to practitioners skilled in this art. Accordingly, it is intended that the scope of the invention be defined by the following claims and their equivalents. Furthermore, it is contemplated that a particular feature described either individually or as part of an embodiment can be combined with other individually described features, or parts of other embodiments. Thus, the absence of describing combinations of such does not preclude the inventor from claiming rights to such combinations.

What is claimed is:

1. A method of monitoring viral safety status associated with entry into a facility, the method comprising:

receiving, at a display user interface rendered at a mobile computing device, a selection of indicia representative of the facility;

receiving, responsive to the selection, an ozone gas viral cleaning status of the facility;

determining, based on the ozone gas viral cleaning status and at least one threshold entrant condition in association with an entrant category, a suitability for entrance into the facility;

initiating an enhanced rate of ozone gas generation for viral cleaning within the facility that shortens a waiting time before a permitted person of the entrant category can enter the facility, the enhanced rate being generated based on at least one of a plurality ozone gas generating devices increasing a rate of ozone gas generation in accordance with switching from a first mode to a second mode of ozone gas generation, the second mode of ozone gas generation being associated with a higher rate of generation of ozone gas than the first mode; and generating, at the display user interface, a notification in accordance with the suitability for entrance.

2. The method of claim 1 wherein the facility comprises one of an at least partially enclosed building, a mobile facility, a vehicle, and a transportation machinery.

3. The method of claim 1 wherein the viral safety status associated with entry comprises at least one of: a time period prior to an attempted entry into the facility, a time period upon entry into the facility and a time period while within the facility.

4. The method of claim 1 wherein the ozone gas viral cleaning status of the facility comprises an ozone gas concentration level within the facility.

5. The method of claim 1 wherein the entrant category comprises at least one of: an adult person, a child, a person attired in protective gear, and an animal.

6. The method of claim 1 wherein the suitability for entrance in accordance with a range of ozone gas concentration as defined by an upper and a lower threshold limits of ozone gas concentration.

7. The method of claim 6 wherein the upper threshold limit is 500 parts per billion (ppb) and the lower threshold limit is 50 ppb of ozone gas concentration.

8. The method of claim 1 wherein the notification comprises, in conjunction with identification of at least one entrant category, one of: a permission to enter, a prohibition against entry, and an estimated time period prior to receiving permission to enter the facility.

9. The method of claim 8 wherein the prohibition against entry includes confirmation of an entrance lockout state being initiated and the estimated time period prior to receiving permission relates to termination of the entrance lockout state.

10. The method of claim 8 wherein the notification comprises a prohibition against entry, and further comprising generating, at the display user interface, a request for permission to enter the facility at an earliest time of achieving suitability for entrance.

11. A mobile computing device comprising:

a processor; and a non-transitory memory including instructions, the instructions when executed by the processor causing the processor to perform operations comprising:

receiving, at a display user interface rendered at the mobile computing device, a selection of an indicia representative of the facility;

receiving, responsive to the selection, an ozone gas viral cleaning status of the facility;

determining, based on the ozone gas viral cleaning status and at least one threshold entrant condition in association with an entrant category, a suitability for entrance into the facility;

initiating an enhanced rate of ozone gas generation for viral cleaning within the facility that shortens a waiting time before a permitted person of the entrant category can enter the facility, the enhanced rate being generated based on at least one of a plurality ozone gas generating devices increasing a rate of ozone gas generation in accordance with switching from a first mode to a second mode of ozone gas generation, the second mode of ozone gas generation being associated with a higher rate of generation of ozone gas than the first mode; and generating, at the display user interface, a notification in accordance with the suitability for entrance.

12. The mobile computing device of claim 11 wherein the facility comprises one of an at least partially enclosed building, a mobile facility, a vehicle, and a transportation machinery.

13. The mobile computing device of claim 11 wherein the viral safety status associated with entry comprises at least one of: a time period prior to an attempted entry into the facility, a time period upon entry into the facility and a time period while within the facility.

14. The mobile computing device of claim 11 wherein the ozone gas viral cleaning status of the facility comprises an ozone gas concentration level within the facility.

15. The mobile computing device of claim 11 wherein the entrant category comprises at least one of: an adult person, a child, a person attired in protective gear, and an animal.

16. The mobile computing device of claim 11 wherein the suitability for entrance in accordance with a range of ozone gas concentration as defined by an upper and a lower threshold limits of ozone gas concentration.

17. The mobile computing device of claim 16 wherein the upper threshold limit is 500 parts per billion (ppb) and the lower threshold limit is 50 ppb of ozone gas concentration.

18. The mobile computing device of claim 11 wherein the notification comprises, in conjunction with identification of at least one entrant category, one of: a permission to enter, a prohibition against entry, and an estimated time period prior to receiving permission to enter the facility.

19. The mobile computing device of claim 18 wherein the prohibition against entry includes confirmation of an entrance lockout state being initiated and the estimated time period prior to receiving permission relates to termination of the entrance lockout state.

20. The mobile computing device of claim 18 wherein the notification comprises a prohibition against entry, and further comprising generating, at the display user interface, a request for permission to enter the facility at an earliest time of achieving suitability for entrance.

* * * * *